United States Patent
Jones et al.

(10) Patent No.: US 8,921,768 B2
(45) Date of Patent: Dec. 30, 2014

(54) SPECTROSCOPIC NANOSENSOR LOGGING SYSTEMS AND METHODS

(75) Inventors: Christopher M. Jones, Houston, TX (US); Michael T. Pelletier, Houston, TX (US); Jing Shen, Houston, TX (US); Marian L. Morys, Downingtown, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/636,294

(22) PCT Filed: Jun. 1, 2011

(86) PCT No.: PCT/US2011/038693
§ 371 (c)(1),
(2), (4) Date: Sep. 20, 2012

(87) PCT Pub. No.: WO2011/153190
PCT Pub. Date: Dec. 8, 2011

(65) Prior Publication Data
US 2013/0068940 A1     Mar. 21, 2013

Related U.S. Application Data

(60) Provisional application No. 61/350,365, filed on Jun. 1, 2010.

(51) Int. Cl.
| | |
|---|---|
| *G01V 5/00* | (2006.01) |
| *G01V 5/04* | (2006.01) |
| *E21B 47/10* | (2012.01) |
| *B82Y 30/00* | (2011.01) |
| *G01N 21/65* | (2006.01) |
| *E21B 49/00* | (2006.01) |

(52) U.S. Cl.
CPC .......... *E21B 47/102* (2013.01); *B82Y 30/00* (2013.01); *G01V 5/00* (2013.01); *G01N 21/658* (2013.01); *E21B 49/00* (2013.01)
USPC ............ 250/253; 250/256; 250/259; 250/255

(58) Field of Classification Search
CPC ........ B82Y 30/00; B82Y 15/00; B82Y 20/00; G01N 21/658
USPC .......................................... 250/253
See application file for complete search history.

(56) References Cited

U.S. PATENT DOCUMENTS

| | | | |
|---|---|---|---|
| 2,972,251 | A | 2/1961 | Harper |
| 4,160,929 | A | 7/1979 | Thorington et al. |

(Continued)

FOREIGN PATENT DOCUMENTS

| | | |
|---|---|---|
| AU | 2009356978 | 6/2011 |
| GB | 177816 | 3/1922 |

(Continued)

OTHER PUBLICATIONS

Geng et al., Suppressed electron hopping in a Au nanoparticle/H2S system: development towards a H2S nanosensor, Feb. 2005, Chemical Commuminications, Issue 14, pp. 1895-1897.*

(Continued)

*Primary Examiner* — David Porta
*Assistant Examiner* — Jeremy S Valentiner
(74) *Attorney, Agent, or Firm* — Krueger Iselin LLP; Benjamin Fite

(57) ABSTRACT

Logging systems and methods that employ nanosensors to obtain spectral measurements downhole. The nanosensors can be dispersed in borehole fluids (including cement slurries) that circulate, diffuse, or get injected in a borehole. Because the nanosensors have diameters on the order of 10 nm to 1000 nm, they readily penetrate into cracks, pores, and other voids where their carrier fluids can reach. The nanosensors transport light sources and recording media to measure spectra in these otherwise inaccessible regions. The nanosensors are then recovered and analyzed to reconstruct the measured spectra and determine relevant material characteristics. Among other things, spectral measurements can reveal the presence of certain elements and molecules in the formation and fluids, from which information scientists determine composition and phases of formation fluids and the formation itself. Certain triggering criteria may also be employed to enable the nanosensor measurements to be associated with specific locations, paths, and/or events.

20 Claims, 3 Drawing Sheets

(56) References Cited

U.S. PATENT DOCUMENTS

| | | |
|---|---|---|
| 4,802,761 A | 2/1989 | Bowen et al. |
| 4,839,516 A | 6/1989 | Freeman et al. |
| 4,994,671 A | 2/1991 | Safinya et al. |
| 4,996,421 A | 2/1991 | Rai et al. |
| 5,161,409 A | 11/1992 | Hughes et al. |
| 5,166,747 A | 11/1992 | Schroeder et al. |
| 5,258,620 A | 11/1993 | Sueyasu et al. |
| 5,284,054 A | 2/1994 | Loebach |
| 5,331,399 A | 7/1994 | Tank et al. |
| 5,341,207 A | 8/1994 | Tank et al. |
| 5,360,738 A | 11/1994 | Jones et al. |
| 5,457,259 A | 10/1995 | Elgarhy et al. |
| 5,621,523 A | 4/1997 | Oobayashi et al. |
| 5,790,432 A | 8/1998 | Morys |
| 5,939,717 A | 8/1999 | Mullins |
| 5,946,641 A | 8/1999 | Morys |
| 6,040,191 A | 3/2000 | Grow |
| 6,162,766 A | 12/2000 | Muir et al. |
| 6,178,815 B1 | 1/2001 | Felling et al. |
| 6,268,726 B1 | 7/2001 | Prammer et al. |
| 6,325,146 B1 | 12/2001 | Ringgenberg et al. |
| 6,350,986 B1 | 2/2002 | Mullins et al. |
| 6,362,619 B2 | 3/2002 | Prammer et al. |
| 6,378,364 B1 | 4/2002 | Pelletier et al. |
| 6,403,949 B1 | 6/2002 | Davis et al. |
| 6,437,326 B1 | 8/2002 | Yamate et al. |
| 6,446,719 B2 | 9/2002 | Ringgenberg et al. |
| 6,446,720 B1 | 9/2002 | Ringgenberg et al. |
| 6,465,775 B2 | 10/2002 | Mullins et al. |
| 6,518,756 B1 | 2/2003 | Morys et al. |
| 6,527,052 B2 | 3/2003 | Ringgenberg et al. |
| 6,543,281 B2 | 4/2003 | Pelletier et al. |
| 6,583,621 B2 | 6/2003 | Prammer et al. |
| 6,688,176 B2 | 2/2004 | Storm et al. |
| 6,729,398 B2 | 5/2004 | Ringgenberg et al. |
| 6,748,328 B2 | 6/2004 | Storm et al. |
| 6,755,079 B1 | 6/2004 | Proett et al. |
| 6,765,384 B2 | 7/2004 | Morys |
| 6,768,105 B2 | 7/2004 | Mullins et al. |
| 6,825,659 B2 | 11/2004 | Prammer et al. |
| 6,888,127 B2 | 5/2005 | Jones et al. |
| 6,912,904 B2 | 7/2005 | Stomr, Jr. et al. |
| 6,956,204 B2 | 10/2005 | Dong et al. |
| 6,967,722 B2 | 11/2005 | Manning |
| 6,975,112 B2 | 12/2005 | Morys et al. |
| 7,021,375 B2 | 4/2006 | Ringgenberg et al. |
| 7,073,579 B2 | 7/2006 | Ringgenberg et al. |
| 7,086,463 B2 | 8/2006 | Ringgenberg et al. |
| 7,095,012 B2 | 8/2006 | Fujisawa et al. |
| 7,195,731 B2 | 3/2007 | Jones |
| 7,245,382 B2 | 7/2007 | Ronnekleiv |
| 7,248,370 B2 | 7/2007 | Jones |
| 7,251,037 B2 | 7/2007 | Jones |
| 7,251,565 B2 | 7/2007 | Storm et al. |
| 7,280,214 B2 | 10/2007 | DiFoggio et al. |
| 7,315,377 B2 | 1/2008 | Holland et al. |
| 7,337,660 B2 | 3/2008 | Ibrahim et al. |
| 7,347,267 B2 | 3/2008 | Morys et al. |
| 7,362,422 B2 | 4/2008 | DiFoggio et al. |
| 7,423,258 B2 | 9/2008 | DiFoggio et al. |
| 7,490,428 B2 | 2/2009 | Morys |
| 7,490,664 B2 | 2/2009 | Skinner et al. |
| 7,508,506 B2 | 3/2009 | Christian et al. |
| 7,511,819 B2 | 3/2009 | DiFoggio |
| 7,511,823 B2 | 3/2009 | Schultz et al. |
| 7,532,129 B2 | 5/2009 | Radzinski |
| 7,571,644 B2 | 8/2009 | Ibrahim et al. |
| 7,579,841 B2 | 8/2009 | San Martin et al. |
| 7,581,435 B2 | 9/2009 | Pelletier |
| 7,696,756 B2 | 4/2010 | Morys et al. |
| 7,697,141 B2 | 4/2010 | Jones et al. |
| 7,762,131 B2 | 7/2010 | Ibrahim et al. |
| 7,775,276 B2 | 8/2010 | Pelletier et al. |
| 7,784,350 B2 | 8/2010 | Pelletier |
| 7,800,513 B2 | 9/2010 | Morys |
| 7,866,387 B2 | 1/2011 | van Zuilekom et al. |
| 7,875,455 B1* | 1/2011 | Li et al. ............ 436/28 |
| 7,938,175 B2 | 5/2011 | Skinner et al. |
| 7,958,936 B2 | 6/2011 | McGregor et al. |
| 7,976,780 B2 | 7/2011 | Elrod et al. |
| 8,037,935 B2 | 10/2011 | Pelletier |
| 8,212,568 B2 | 7/2012 | Morys et al. |
| 8,237,920 B2 | 8/2012 | Jones et al. |
| 2001/0016562 A1* | 8/2001 | Muir et al. ............ 507/201 |
| 2004/0164237 A1 | 8/2004 | Jones et al. |
| 2005/0005694 A1 | 1/2005 | Jones et al. |
| 2005/0019955 A1* | 1/2005 | Dahl et al. ............ 436/524 |
| 2005/0052105 A1 | 3/2005 | Schmidt |
| 2005/0099618 A1 | 5/2005 | DiFoggio et al. |
| 2005/0169348 A1* | 8/2005 | Chen et al. ............ 374/161 |
| 2006/0142955 A1 | 6/2006 | Jones et al. |
| 2007/0035736 A1 | 2/2007 | Vannuffelen et al. |
| 2007/0103162 A1 | 5/2007 | Morys et al. |
| 2007/0259433 A1 | 11/2007 | Jones et al. |
| 2008/0099241 A1 | 5/2008 | Ibrahim et al. |
| 2008/0125335 A1* | 5/2008 | Bhavsar ............ 507/219 |
| 2008/0202747 A1 | 8/2008 | Gleitman et al. |
| 2008/0297808 A1 | 12/2008 | Riza et al. |
| 2009/0107667 A1* | 4/2009 | Mullins et al. ............ 166/250.12 |
| 2009/0120637 A1* | 5/2009 | Kirkwood et al. ............ 166/254.2 |
| 2009/0151939 A1* | 6/2009 | Bailey et al. ............ 166/255.1 |
| 2009/0199630 A1 | 8/2009 | DiFoggio et al. |
| 2009/0288820 A1* | 11/2009 | Barron et al. ............ 166/249 |
| 2010/0148787 A1 | 6/2010 | Morys et al. |
| 2010/0231225 A1 | 9/2010 | Morys et al. |
| 2010/0245096 A1 | 9/2010 | Jones et al. |
| 2010/0265094 A1 | 10/2010 | Zannoni et al. |
| 2011/0023583 A1 | 2/2011 | Jones et al. |
| 2011/0023594 A1 | 2/2011 | Pelletier et al. |
| 2011/0031972 A1 | 2/2011 | Pelletier et al. |
| 2011/0218736 A1 | 9/2011 | Pelletier |
| 2011/0251794 A1 | 10/2011 | Bittar et al. |
| 2012/0018152 A1 | 1/2012 | Zuilekom et al. |
| 2012/0018167 A1 | 1/2012 | Konopczynski et al. |
| 2012/0084021 A1 | 4/2012 | Jones et al. |
| 2012/0150451 A1 | 6/2012 | Skinner et al. |
| 2012/0160018 A1 | 6/2012 | Jones et al. |
| 2012/0211650 A1 | 8/2012 | Jones et al. |
| 2012/0223221 A1 | 9/2012 | Jones et al. |
| 2012/0232707 A1 | 9/2012 | Jones et al. |
| 2012/0250017 A1 | 10/2012 | Morys et al. |
| 2013/0109100 A1* | 5/2013 | Sarkar et al. ............ 436/27 |

FOREIGN PATENT DOCUMENTS

| | | |
|---|---|---|
| GB | 310895 | 10/1930 |
| GB | 1088268 | 10/1967 |
| GB | 2441069 | 2/2008 |
| GB | 2493652 | 2/2013 |
| WO | WO-2011/063086 | 5/2011 |
| WO | WO-2011/078869 | 6/2011 |
| WO | WO-2011/153190 | 12/2011 |
| WO | WO-2011/159289 | 12/2011 |
| WO | WO-2011159294 | 12/2011 |
| WO | WO-2012/161693 | 11/2012 |

OTHER PUBLICATIONS

Adur, Rohan "Using Single Nitrogen-Vacancy Centers in Diamond Nanocrystals for Sensitive Sensing of Weak Magnetic Fields with Nanoscale Resolution", Ohio State Physics Term Paper, circa 2009, 4 pgs.

Alaskar, Mohammed et al., "In-Situ Multifunction Nanosensors for Fractured Reservoir Characterization", Proceedings, Thirty-fifth Workshop on Geothermal Reservoir Engineering, Stanford University, Stanford, California, Feb. 1-3, 2010, SGP-TR-188. Retrieved from the Internet <http://ere.stanford.edu/pdf/IGAstandard/SGW/2010/askar.pdf>., 13 pgs.

Balasubramanian, Gopalakrishnan et al., "Nanoscale Imaging Magnetometry with Diamond Spins under Ambient Conditions", Nature, vol. 455, Oct. 2, 2008, pp. 648-651.

Bleier, Z et al., "A Monolithic Interferometer for FT-IR Spectroscopy", Spectroscopy, 13 (10), pp. 46-49. (Oct. 1999).

(56) References Cited

OTHER PUBLICATIONS

Boudou, J.P. et al., "High Yield Fabrication of Fluorescent Nanodiamonds", Nanotechnology v20 n23, Jun. 10, 2009, 11 pgs.

Dumeige, Y. et al., "Photo-Induced Creation of Nitrogen-Related Color Centers in Diamond Nanocrystals Under Femtosecond Illumination", Elsevier, www.elsevier.com/locate/jlumin, Journal of Luminescence 109 (2004), pp. 61-67.

Faklaris, Orestis et al., "Comparison of the Photoluminescence Properties of Semiconductor Quantum Dots and Non-Blinking Diamond Nanoparticles. Observation of the Diffusion of Diamond Nanoparticlesin Living Cells", J. European Optical Society, v4, 2009, 8 pgs.

Florescu, Marian et al., "Improving Solar Cell Efficiency Using Photonic Band-Gap Materials", ScienceDirect.com, (Jun. 29, 2007), pp. 1599-1610.

ICX Photonics, "markIR Infrared Emitters", icxphotonics.com, ICx Photonics, pp. 1-2.

Lee, Seung W., et al., "A Soluble Photoreactive Polyimide Bearing the Coumarin Chromophore in the Side Group: Photoreaction, Photoinduced Molecular Reorientation, and Liquid-Crystal Alignability in Thin Films", Langmuir 19 (24) 2003, pp. 10381-10389.

Rabeau, J. R., et al., "Single Nitrogen Vacancy Centers in Chemical Vapor Deposited Diamond Nanocrystals", Nano Letters, v7 n11 p3433-3437, 2007, Macquarie University, New South Wales 2109, Australia., pp. 1-20.

Simons, J. K., et al., "X-ray Energy Dependent Photochemestry of the Adamantane (C10H16)/Si(111)-7X7 Surface", American Vacuum Society, J. Vac Sci. Technol. A 11(4) Jul./Aug. 1993, pp. 2244-2249.

Sonnefraud, Yannick et al., "25-nm Diamond Crystals Hosting Single NV Color Centers Sorted by Photon-Correlation Near-field Microscopy", Optics Letters, vol. 33, Issue 6, 2008, pp. 611-613.

Tank, V. "Remote Detection and Quantification of Hot Molecular Combustion Products—Experimental Instrumentation and Determination of Optimal Infrared Spectral Micro Windows", Journal of Molecular Structure, vol. 744-747, 3, pp. 235-242, (2005).

Tisler, Julia et al., "Fluorescence and Spin Properties of Defects in Single Digit Nanodiamonds", American Chemical Society, ACS Nano v3 n7 p1959-1965, 2009, pp. 1959-1965.

Van Der Sar, T. et al., "Nanopositioning of a Diamond Nanocrystal Containing a Single NV Defect Center", Applied Physics Letters v94 n17, 2009, 3 pgs.

Zhang, Wei et al., "Method to Increase the Number of Filters per Optical Path in a Downhole Spectrometer", PCT Appl No. PCT/US11/037655, filed May 24, 2011, 12 pgs, (Nov. 2012).

Zhang, Wei et al., "Method to Increase the Numbers of Filters per Optical Path in a Downhole Spectrometer", International Search Report and Written Opinion, filed May 24, 2011, 10 pgs, (Nov. 2012).

PCT International Preliminary Report on Patentability, dated Dec. 13, 2012, Application No. PCT/US2011/038693, "Spectroscopic Nanosensor Logging Systems and Methods", filed Jun. 1, 2011, 9 pgs.

First Chinese Office Action, dated Feb. 5, 2013, Appl No. 200980157701.3, "Interferometry-Based Downhole Analysis Tool", filed Dec. 23, 2009, 13 pgs.

US Non-Final Office Action, dated Mar. 26, 2013, U.S. Appl. No. 13/147,478, "Interferometry-Based Downhole Analysis Tool", filed Dec. 23, 2009, 18 pgs.

Canadian Examiner Letter, dated Oct. 24, 2012, Appl No. 2,756,285, "Interferometry-Based Downhole Analysis Tool", filed Dec. 23, 2009, 2 pgs.

US Final Office Action, dated May 31, 2013, U.S. Appl. No. 13/147,478, "Interferometry-Based Downhole Analysis Tool", filed Dec. 23, 2009, 18 pgs.

US Non-Final Office Action, dated Sep. 24, 2013, U.S. Appl. No. 13/147,478, "Interferometry-Based Downhole Analysis Tool", filed Dec. 23, 2009, 22 pgs.

European Search Report, dated Dec. 12, 2013, Appl No. 09852686.6, "Interferometry-Based Downhole Analysis Tool", filed Dec. 23, 2009, 7 pgs.

US Final Office Action, dated Apr. 4, 2014, U.S. Appl. No. 13/147,478, "Interferometry-Based Downhole Analysis Tool," filed Aug. 2, 2014, 25 pgs.

CN Notice on the First Office Action, dated Aug. 15, 2014, Appl. No. 201180025452.X, "Spectroscopic Nanosensor Logging Systems and Methods," Filed Jun. 1, 2011, 52 pgs.

\* cited by examiner

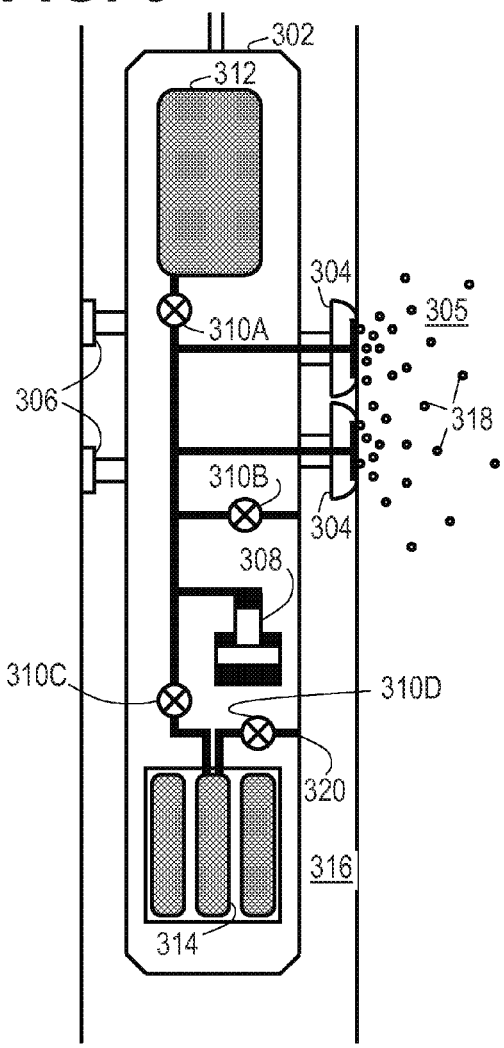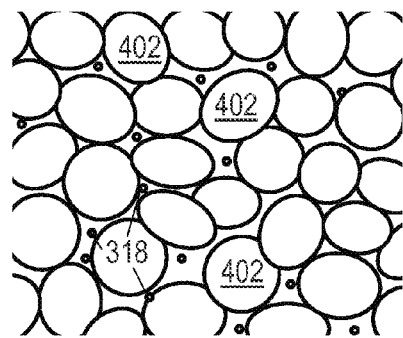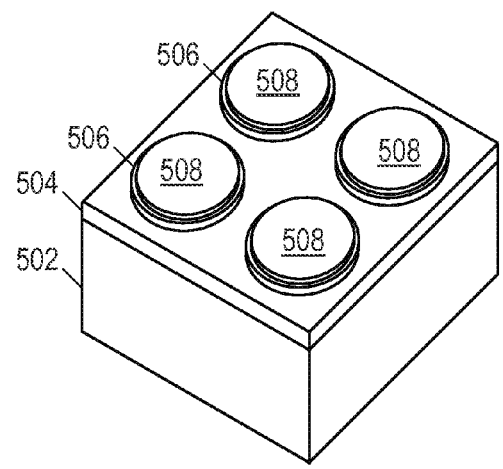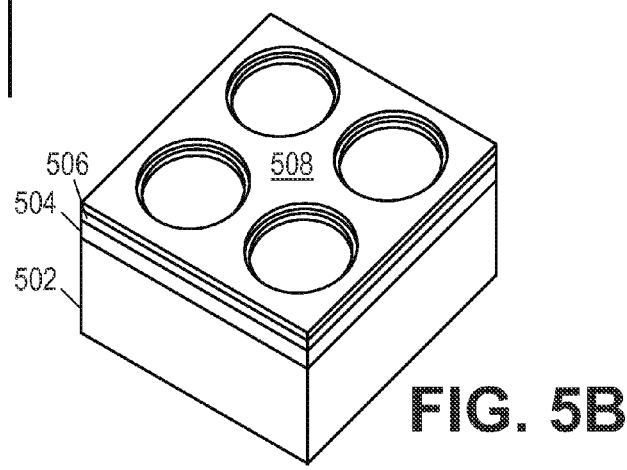

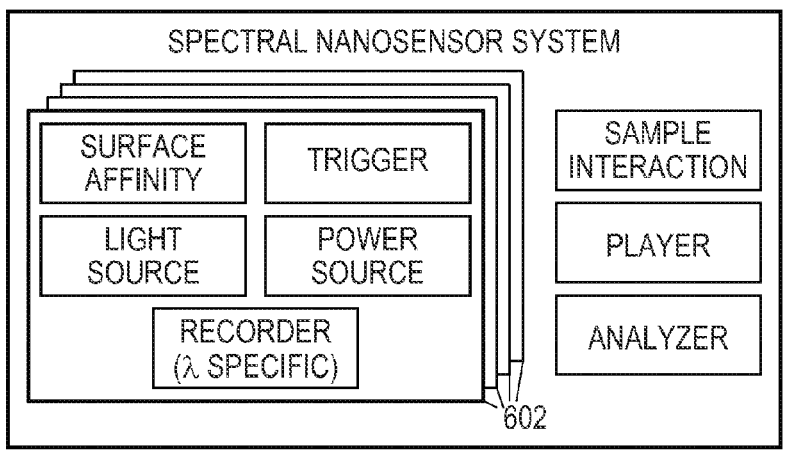
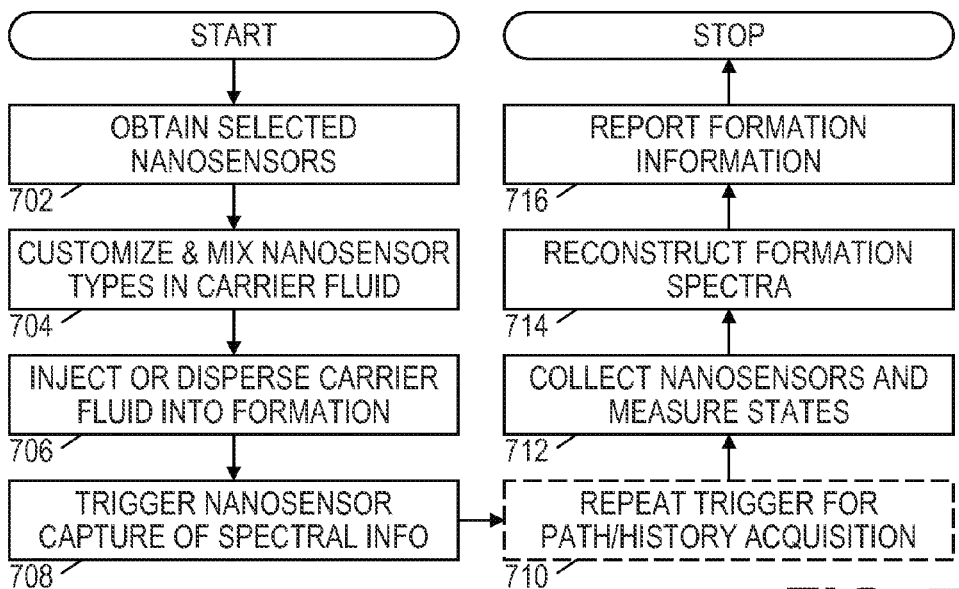

SPECTROSCOPIC NANOSENSOR LOGGING SYSTEMS AND METHODS

CROSS-REFERENCE TO RELATED APPLICATIONS

This application claims priority to Provisional U.S. Application 61/350,365, titled "OILFIELD SYSTEMS AND METHODS USING SPECTROSCOPIC NANOSENSORS, and filed Jun. 1, 2010, by Christopher M. Jones, Michael T. Pelletier, Jing (Cynthia) Shen, and Marian L. Morys, which is hereby incorporated herein by reference.

BACKGROUND

Modern oil field operators demand access to a great variety of information regarding the parameters and conditions encountered downhole. Such information typically includes characteristics of the earth formations traversed by the borehole and data relating to the size and configuration of the borehole itself. The collection of information relating to conditions downhole, which commonly is referred to as "logging," is typically performed by wireline logging, tubing-conveyed logging, and/or "logging while drilling" (LWD). In any one of these methods, the tools can obtain samples of reservoir rock and fluids and analyze them in the borehole or convey them to the surface for analysis. Alternatively, the tools can conduct near-borehole measurements using acoustic energy, electromagnetic signals, nuclear radiation, etc. Each of these techniques suffer from various limitations. For example, samples taken to surface may retain a history of changing condition effects, e.g., pressure and temperature changes that cause degradation of the sample. Contact with the tool or other borehole fluid can also cause chemical degradation of the sample. Even pulling fluids from the formation into the tool often induces some irreversible changes to, e.g., $H_2S$ concentration level or asphalting particle size. These and other logging techniques may be unable to adequately account for formation inhomogeneities as they collect their measurements. Under these circumstances clients are forced to reconstruct the history of changes to derive what down hole measurements might have yielded. Inadequate understanding of the formation characteristics can lead to financial allocation errors and very costly production modifications.

DESCRIPTION OF THE DRAWINGS

A better understanding of the various disclosed embodiments can be obtained when the following, detailed description is considered in conjunction with the attached drawings, in which:

FIG. 3 shows an illustrative formation fluid sampler;

FIG. 4 shows an illustrative formation configuration;

FIGS. 5A-5B show illustrative nanosensor constructions;

FIG. 6 is a function block diagram of an spectral nanosensor system; and

FIG. 7 is a flow diagram of a logging method that employs spectroscopic nanosensors.

Figure 1:
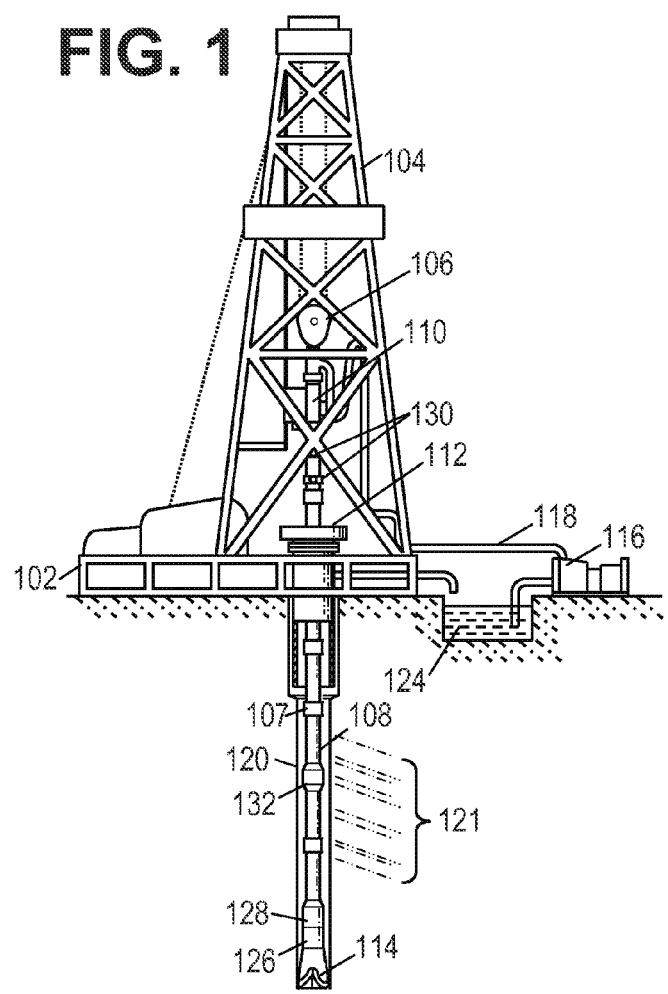
FIG. 1 shows an illustrative environment for logging while drilling ("LWD")

While the invention is susceptible to various modifications and alternative forms, specific embodiments thereof are shown by way of example in the drawings and will herein be described in detail. It should be understood, however, that the drawings and detailed description thereto are not intended to limit the disclosure to the particular illustrated embodiments, but on the contrary, the intention is to cover all modifications, equivalents and alternatives falling within the scope of the appended claims.

DETAILED DESCRIPTION

Accordingly, there are disclosed herein various logging systems and methods that employ nanosensors to obtain spectral measurements downhole. The nanosensors can he dispersed in borehole fluids (including cement slurries) that circulate, diffuse, get injected, or otherwise get exposed to the formation, formation fluids, or other materials of interest. Because the nanosensors have diameters on the order of 10 nm to 1000 nm, they readily penetrate into cracks, pores, and other voids where their carrier fluids can reach. The nanosensors transport light sources and recording media to measure spectra in these otherwise inaccessible regions. The nanosensors are then recovered and the recording media analyzed to reconstruct the measured spectra and determine relevant material characteristics therefrom. Among other things, spectral measurements can reveal the presence of certain elements and molecules in the formation and fluids, from which information scientists may be able to determine composition and phases of formation fluids and the formation itself. Certain triggering criteria may also be employed to add other dimensions to the measurements, e.g., different time delays, pressure thresholds, temperature thresholds, field strengths. Such triggering criteria can enable the nanosenor measurements to be associated with specific locations, paths, and/or events.

Thus, spectroscopic nanosensors offer a way to acquire reservoir description information from within the reservoir. Acquired information could include measurements related to chemical and physical properties of fluids or rocks as they lie nascent at a distance from any boreholes. Spectroscopic nanosensors can be incorporated into systems for: measurement while drilling, mud measurements, formation testing tools, production enhancement including improved oil recovery or fracture jobs, stimulation jobs including acid treatments, and coiled tubing treatments. The nanoscale sensors can be easily transported by carrier fluids into relatively permeable formations to obtain spectroscopic measurements of materials that they contact. The carrier fluid can be a component of a borehole fluid such as a drilling fluid, a stimulation or chemical treatment fluid, a flood/injection fluid, or a reverse pumpout formation test fluid. The spectroscopic nanosensors can be later recovered (either downhole or at the surface) in a number of ways, including pumpout or natural flow of the injected zone. Downhole tools can interrogate the nanosensors or the interrogation can be performed at the surface.

The disclosed systems and methods are best understood in the context of a suitable usage environment. Accordingly, FIG. 1 shows an illustrative logging while drilling (LWD) environment, A drilling platform 102 supports a derrick 104 having a traveling block 106 for raising and lowering a drill string 108. A top drive 110 supports and rotates the drill string 108 as the string is lowered through a well head 112. The drill string's rotation (and/or a downhole motor) drives a drill bit 114 to extend the borehole through subsurface earth formations 121. Mud recirculation equipment 116 draws drilling fluid from a retention pit 124 and pumps it through a feed pipe 118 to top drive 110, through the interior of drill string 108 to the drill bit 114, through orifices in drill bit, through the annulus around drill string 108 to a blowout preventer at the surface, and through a discharge pipe into the pit 124. The drilling fluid transports cuttings from the borehole into the pit 124 and aids in maintaining the borehole integrity.

One or more logging tools 126 are integrated into the bottom-hole assembly near the bit 114. Suitable logging tools include formation fluid sampling tools, acoustic logging tools, electromagnetic resistivity tools, and nuclear magnetic resonance tools, among others. Logging while drilling tools usually take the form of a drill collar, i.e., a thick-walled tubular that provides weight and rigidity to aid the drilling process. As the bit extends the borehole through the formations, the logging tool(s) collect measurements of formation characteristics. Other tools and sensors can also be included in the bottomhole assembly to gather measurements of various drilling parameters such as position, orientation, weight-on-bit, borehole diameter, etc. Control/telemetry module 128 collects data from the various bottomhole assembly instruments (including position and orientation information) and stores them in internal memory. Selected portions of the data can be communicated to surface receivers 130 by, e.g., mud pulse telemetry. Other logging-while drilling telemetry methods also exist and could be employed. For example, electromagnetic telemetry or through-wall acoustic telemetry can be employed with an optional repeater 132 to extend the telemetry range. As another example, the drill string 108 could be formed from wired drillpipe that enables waveforms or images to be transmitted to the surface in real time to enable quality control and processing to optimize the logging resolution. Most telemetry systems also enable commands to be communicated from the surface to the control and telemetry module to configure the operation of the tools.

Figure 2:
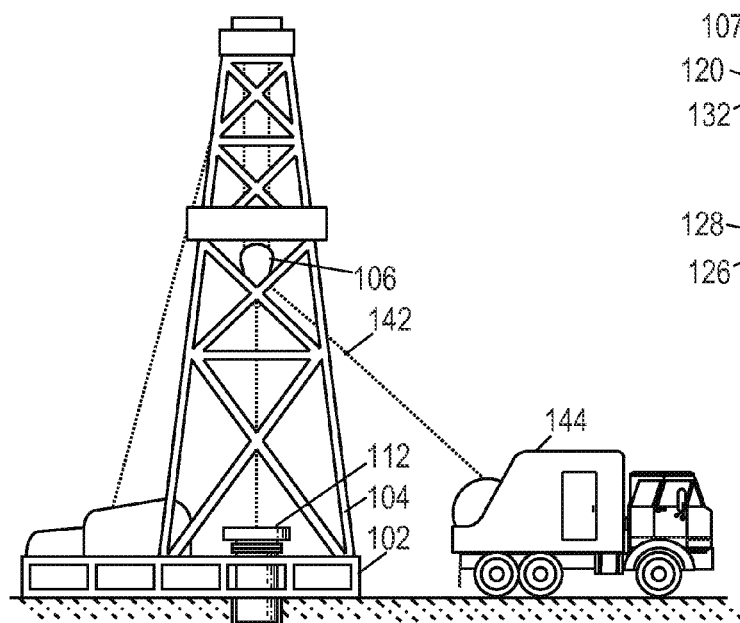
FIG. 2 shows an illustrative environment for wireline logging.
Figure 2:
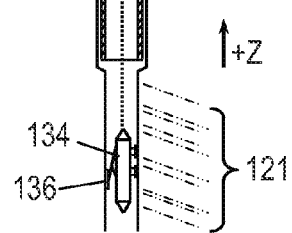

At various times during the drilling process, the drill string 108 may be removed from the borehole as shown in FIG. 2. Once the drill string has been removed, logging operations can be conducted using a wireline logging tool 134, i.e., a sensing instrument sonde suspended by a cable 142 having conductors for transporting power to the tool and telemetry from the tool to the surface. The wireline logging tool 134 may have pads 136 and/or centralizing springs to maintain the tool near the axis of the borehole as the tool is pulled uphole. As explained further below, tool 134 can include formation fluid sampling, acoustic logging, electromagnetic resistivity, and/or NMR logging instruments. A logging facility 144 collects measurements from the logging tool 134, and includes a computer system for processing and storing the measurements gathered by the logging tool.

As previously mentioned, there are a number of ways in which the nanosensors can be introduced into the downhole environment including, e.g., in a drilling fluid, a cement slurry, and a treatment/stimulation fluid. Where a more targeted use of nanosensors is desired, a portion of the borehole or borehole wall can he isolated for exposure to the nanosensors.

FIG. 3 shows an illustrative downhole fluid sampler 302 for wireline use. The illustrative fluid sampler 302 has been adapted to employ spectroscopic nanosensors. The sampling tool 302 includes one or more probes 304 terminated by cup-shaped sealing pads for contacting the borehole wall. Arms 306 extend from the tool opposite from the probes 304 to contact the borehole wall and force the tool to hold the probes in tight contact with the formation 305. The probes 304 are coupled via internal flow lines to a piston pump 308 that operates in cooperation with a set of valves 310 to move fluid between an internal reservoir 312, the formation 305, sample chambers 314, and the borehole annulus 316. With careful coordination of the piston's direction and the configuration of valves 310, the pump can draw a volume of nanosensor-laden carrier fluid from reservoir 312 and force it into the formation 305, causing nansensors 318 to diffuse through the cracks, pores, and voids of the formation. After a triggering event (discussed further below), the pump can withdraw a volume of fluid from the formation 305 and deposit it in one of the sample chambers 314 along with any entrained nanosensors. Multiple sample chambers 314 can be included in a rotating cartridge to enable multiple samples to be captured at different times and, if desired, at different locations in the borehole. An additional port 320 is provided to enable fluids to be sampled from or exhausted to the borehole annulus 316. The sequence in which fluids are withdrawn from or injected to the formation, the reservoir, the sample chambers, and the borehole annulus can be varied as desired by the operator.

FIG. 4 shows an illustrative formation cross-section having large grains 402 conglomerated in such a fashion as to leave small interstitial voids filled with fluids of a liquid and/or gas variety. Of course, rock formations vary and their voids can have many shapes and variations. In any event, it is expected that most formations will have voids large enough for nanosensors 318 to enter and penetrate deeply into the rock.

FIG. 5A shows an illustrative spectroscopic nanosensor construction in which a substrate 502 is provided with a luminescent layer 504, areas of which are replaced by or covered with a photosensitive layer 508. The luminescent layer 504 is separated from the photosensitive layer 508 by an opaque layer or region 506 to prevent direct transmission of photons from the luminescent regions to the photosensitive regions. The illustrated construction in FIG. 5A employs a pattern of circular photosensitive islands over a continuous luminescent layer, but other constructions are also operational for the desired effect. FIG. 5B, for example, shows a photosensitive layer 508 having a pattern of circular holes through which regions of the luminescent layer 504 are revealed. An opaque layer 506 separates the other two layers to prevent direct transmission of light from the luminescent layer to the photosensitive layer. In other constructions, stripes or bands of photosensitive material are interspersed with stripes of luminescent material, with opaque material between the stripes to ensure that the light which strikes the photosensitive material has been reflected or scattered from the environment around the nanosensor. The pattern and distribution of the luminescent material can be varied as desired to provide a suitable ratio of illumination area to detection area with suitable separations between the two. A passivation layer may be included on top to protect the deposited layers from oxidation or other undesired chemical interactions, The substrate with the deposited layers can then be ground to a fine powder to provide nanoparticles of the desired sizes.

A variety of luminescent light sources are contemplated. One example employs a diamond film grown on a substrate and subjected to electron bombardment or an ultraviolet light laser treatment to create nitrogen vacancies. When excited by an electromagnetic pulse of the appropriate frequency and strength, the nitrogen vacancies flouresce, thereby illuminating their surroundings. The process for creating nitrogen vacancies can be optimized to maximize photon production for a given electromagnetic trigger pulse, Details on the creation and energizing of such a nanoscale light source can be found in the following references, which are hereby incorporated by reference:

J. P. Boudou et al., "High yield fabrication of fluorescent nanodiamonds", Nanotechnology v20 n23, Jun. 10, 2009.

J. R. Ruben et al, "Single Nitrogen Vacancy Centers in Chemical Vapor Deposited Diamond Nanocrystals", Nano Letters, v7 n11 p 3433-3437, 2007.

R. Adur, "Using single nitrogen-vacancy centers in diamond nanocrystals for sensitive sensing of weak magnetic fields with nanoscale resolution", Ohio State Physics Term Paper, circa 2009.

T. van der Sar et al., "Nanopositioning of a diamond nanocrystal containing a single nitrogen-vacancy defect center", Applied Physics Letters v94 n17, 2009.

Y. Sonnefraud et al., "25-nm diamond nanocrystals hosting single NV color centers sorted by photon-correlation near-field microscopy", Optics Letters, Vol. 33, Issue 6, pp. 611-613 (2008).

O. Faklaris et "Comparison ofpboLobnxdocmconcc properties of semiconductor quantum dots and non-blinking diamond nanoparticles and observation of the diffusion of diamond nanoparticles in cells", J. European Optical Society, v4, 2009.

J. Tisler et al., "Fluorescence and Spin Properties of Defects in Single Digit Nanodiamonds", ACS Nano v3 n7 p 1959-1965, 2009.

Y. Dumeigea et at, "Photo-induced creation of nitrogen-related color centers in diamond nanocrystals under femtosecond illumination", Journal of Luminescence v109 p 61-67 (2004).

G. Balasubramanian et al., "Nanoscale imaging magnetometry with diamond spins under ambient conditions", Nature 455, 648-651 (2 Oct. 2008).

Other luminescent materials are also contemplated for use in the nanosensor systems, including hardy materials that produce light via bioluminescence, chemiluminescence, electroluminescence, phosphorescence, fluorescence, radioluminescence, sonoluminescence, and thermoluminescence. In particular, chemiluminescence is discussed further below as a mechanism for provided a delayed triggering of the nanosensors' data acquisition.

As with the light source materials, a variety of photosensitive materials are contemplated. Sputtered silver halide would provide broadband photon detection. Detection of photons within narrow color bands is obtainable with chromophore-doped polyamide, for color bands. Adamantane with 2, 8 and 9 as the functional groups is also contemplated for use as the photoactive recording medium. Details on the creation and use of chromophore-doped polyimides and adamantane can be found in the following references, which are hereby incorporated by reference:

S. W. Lee et al., "A Soluble Photoreactive Polyimide Bearing the Coumarin Chromophore in the Side Group: Photoreaction, Photoinduced Molecular Reorientation, and Liquid-Crystal Alignability in Thin Films", Langmuir 19 (24), pp 10381-10389, 2003.

J. K. Simons et al., "X-ray energy dependent photochemistry of the adamantane (C10H16)/Si(111)-7×7 surface" J. Vac. Sci. Technol. A v11, n4, p 2244-2249 (July 1993)

Other photosensitive materials are also contemplated for use in the nanosensor systems, including photodegradable molecules that, when exposed, cause tracer chemicals to leak into the surrounding environment.

The film and substrate material is ground to fine powder. It may be evident that some variation is expected and perhaps desirable in the resulting nanosensors. For example, the particle size will vary across some range (e.g., 10 nm to 1000 nm) as well as the particle's shape, the relative orientations and amounts of the luminescent and photosensitive materials, and the temperature and energies at which the electron bombardments occur. The various manufacturing parameters can be optimized via Monte Carlo simulation to get the desired distribution of nanosensor characteristics.

Though the foregoing discussion assumes that each nanoparticle is provided with both a luminescent material and a photosenstive material, it is not strictly necessary to provide each nanosensor with both. Some contemplated system embodiments separate these two functions, so that some fraction of the nanoparticles are equipped with luminescent material and the rest are equipped with photosensitive material.

FIG. 6 is a representation of an illustrative spectroscopic nanosensor system having multiple nanoparticle types 602. The various types 602 can vary in their construction. It is expected that each type will have one or more of the following customizable features: a surface affinity, a trigger, a light source, a power source, and a recorder, which are each discussed below. In addition to the various types of nanoparticles, the system further includes a sample interaction mechanism, a player, and an analyzer.

The custom surface affinity is an optional characteristic that provides the nanoparticle with an increased tendency to interact with a given target in the downhole environment. Specifically, the nanoparticle may be provided with a size, shape, and surface chemistry that enhances the nanoparticle's ability to interact with a selected target such as, e.g., an aqueous phase, a hydrocarbon phase, or a chemical analyte. As one particular example, the surface can be provided with a hydrophilic or hydrophobic coating to increase its solubility in a desired phase, thereby providing the nanoparticle with an enhanced chance of being in contact with the selected target when triggered.

The custom trigger may be a separate component of a nanoparticle type, or it can be an inherent part of how the light source energized. The trigger governs the time(s) at which the nanosensors collect their measurements. It can be given in the form of an externally applied electromagnetic pulse. Alternatively, the trigger can be a time-release membrane. Another alternative is an environmental condition such as, e.g., pH, eH, analyte concentration (or the presence of some other chemical), a temperature threshold, a pressure threshold, vibration, turbulence, magnetic field, or some target combination of conditions such as those that would represent the onset of scaling. In most cases, it is expected that the trigger would cause the light source to illuminate, but it is also contemplated that the trigger would enable the photosensitive material to be exposed.

The light source, as previously discussed, is contemplated to be a luminescent material. Different nanoparticle types could be provided with different luminescent materials. Such variation could, for example, increase the range of wavelengths over which spectroscopic measurements are acquired. Alternatively, or in addition, the variety of luminescent materials could provide different triggering times or conditions, thereby providing one potential mechanism for determining the variation of spectral measurements with respect to time, position, or some other variable.

The power source is an optional part of the nanoparticles, and it can take the form of a chemical mixture that reacts to produce light. It could also take the form of a resonant antenna that converts transmitted electromagnetic energy into power for a light emitting diode, or a junction between dissimilar materials that is energized by heat or ambient ions to generate electricity. It is even contemplated that a small quantity of radioactive material could be employed to induce phosphorescent molecules to glow. In most cases, however, it is expected that an external electromagnetic or sonic field would act directly on the luminescent material to pro vide illumination.

As previously discussed, the recorder can be a photosensitive material that changes state when exposed to light. The photosensitive material can be broadband (such as a silver halide) or wavelength-selective. For a subsequent spectral analysis to be performed, it is expected that either or both of the light source and the photosensitive material will have a relatively narrow band of wavelengths. Some spectral nanosensor types may have both a broadband source and broadband sensitivity to aid in calibrating the spectral measurements acquired by wavelength-specific nanosensor types. In at least some embodiments, the exposed nanosensors release a highly identifiable and unique tracer into the surrounding fluid, causing the flow of that fluid to become the telemetry medium that communicates the measurements to downstream sensors.

The sample interaction mechanism employed by the system is that mechanism that provides the nanosensor system with access to the desired portions of the downhole environment. In a fashion similar to the modified fluid sampling tool of FIG. 3, the mechanism can be designed to expose targeted portions of the formation. Alternatively, the nanosensors can be conveyed throughout the downhole circulation path by a carrier fluid. In some embodiments where the sensors are widely diffused, a wireline or LWD tool can be employed to activate nanosensors within a desired region and to capture at least some of them in a fluid or core sample.

The system's player mechanism extracts the relevant state information from the nanosensors that have been exposed. In some embodiments, the nanosensors release tracer chemicals into their surrounding fluid and the player performs a chemical analysis to detect the relative concentrations of these tracers. In other embodiments, the nanosensors themselves are recaptured, separated from the fluid, and processed to extract their state information. In the case of the diamond nanocrystals described previously, analysis can take the form of the following sequence of operations. The fluid sample is centrifuged to separate the hulk of the liquid from the entrained solids. The sludge is repeatedly washed with an oil solvent substance (e.g., toluene) and re-centrifuged until only solid inorganic residue is left. The other inorganic residue is removed from the nanosensors with a HCl treatment followed by IV treatment (although the order may be reversed the expected order is HCl first followed by HF). At this point, it is expected that only the nanosensors would remain. Their size distribution is analyzed with normal particle size distribution methods, and the state of their photosensitive materials is probed via electron spin resonance (ESR) or optical methods which may require the use of chemicals to develop and fix the state of the photosensitive materials prior to optical examination. Until this probe has been performed, the nanosensors should be isolated from any external light to avoid degrading their measurements. Afterwards, however, the nanosensors may be re-triggered to analyze their luminescence intensity and spectra. This information is combined with the information from the probe operation to reconstruct the far field spectrum observed by the nanosensors. A separate sample of the recovered fluid can be analyzed spectroscopically and compositionally, and the results compared to interpret the state of the nascent reservoir fluids and rocks.

FIG. 7 is a flow diagram of an illustrative logging method that employs spectroscopic nanosensors. It begins in block 702 as the operator obtains the selected nanosensors. As previously discussed, nanosensors can be constructed in various sizes and shapes, and be provided with various luminescent and photosensitive materials. The operator can provide further customization in block 704 by, e.g., further sorting the nanosensors into selected sizes, providing surface coatings, and/or forming a mixture of different nanosensor types designed to obtain the desired spectra measurements. The operator suspends the selected nanosensors in a carrier fluid.

In block 706, the operator injects the carrier fluid with the nanosensors into the formation or circulates the fluid through the borehole to disperse the nanosensors. The nanosensors can even be entrained in a flood fluid that passes from an injection well to a producing well. In block 708, the nanosensors are triggered to acquire their spectral measurements, As previously mentioned, there are a variety of available triggering mechanisms that can be employed to refine the measurements that are acquired by the nanosensors. In optional block 710, the triggering operation may be repeated to cause the nanosensors to acquire additional measurements that enable their path or history to be later reconstructed. Acoustic, EM or pressure pulses can provide reference time markers at predefined intervals. Alone or in combination with a time-based logging mechanism (perhaps using a diffusion process in a substrate to embed the information into a crystal growth or perhaps using a electrochemical deposition process that can be time resolved), these pulses enable the acquired information to be read in away similar to the way in which $CO_2$ concentration is read from ice cores in Antarctica, i.e., layer by layer. Some system embodiments include a mechanism for tracing the nanosensors' location or even their path) in the formation, For example, operators can use focused, steerable sonic or EM beams to trigger only particles at certain locations or at selected distances relative to the borehole. When such spatial triggering is combined with time-based logging, nanosensor path information can be discerned.

In block 712, the operator collects the nanosensors and extracts their state information. In block 714, the operator analyzes the extracted information to reconstruct the spectra observed by the nanosensors. From these spectra, the operator can extrapolate information about the reservoir fluids and rocks, which presented as a report in block 716.

Particular logging examples are now described. In a wireline formation tester example, the tool contacts the borehole wall with a probe. An initial formation pump out is performed to clear near-wellbore contamination including at least the mud cake from the probe's pad. It may be desirable to continue pumping until most of the near-wellbore drilling fluid filtrate contamination has been cleared as well. The pump is then reversed and a carrier fluid containing spectroscopic nanosensors is injected into the formation. The carrier fluid which has been designed to be miscible with the desired sample phase is either allowed to mix with the formation fluid over time, or, is forcibly mixed by oscillating direction of fluid flow. The degree of mixing can be modeled or monitored with sensors in the tool. Once mixing is complete, the nanosensors are triggered. One possible trigger method is to provide power from an external power source. One convenient method of external triggering and powering is an electromagnetic pulse from an NMR tool, which activates a nitrogen-vacancy crystal defect in a diamond nanocrystal and causes the defect to fluoresce. Another method is a sonic pulse designed to disrupt an encapsulated membrane separating two chemicals. When the chemicals combine they undergo a photo-luminescent reaction. Another possible trigger method is the elapsing of an internal timer. For example, the encapsulated membrane between two chemicals may be designed to degrade over time (e.g., such membranes are often employed in time release capsules). As yet another alternative, the sensor is filled with a photo-sonoluminescence material, enabling sound waves to act as both the trigger and the power source.

The light emitted from the nanosensors' light sources interacts with the materials surrounding the nanosensors. Those materials scatter, reflect, or re-emit the light back to the photosensitive material in the nanosensors. The pump draws fluid back from the formation along with the entrained nanosensors and captures at least one sample. The acquired sample may contain mainly the formation fluid. The tool may employ an optimization process to maximize the utility of the samples with regard to sampling the formation fluid and maximizing the concentration of captured nanosensors. The optimization process can employ tool sensors that monitor properties of the fluid and/or the concentration of nanosensors. Some tool embodiments collect the nanosensor information downhole, while other tool embodiments transport the captured fluids and nanosensors to the surface for analysis.

In a reservoir flood example, the nanosensors are manufactured with a time release trigger. The trigger may be a degradable membrane incorporated into the nanosensor shortly before delivery to the well site. The nanosensors are suspended in a carrier fluid phase designed to be miscible with the target sample phase. The carrier fluid is injected with the flood fluid (flood fluid may be liquid or gas). While the flood propagates through the formation, the nanosensors diffuse to the target phase. The time delay trigger degrades, causing a chemical reaction to provide light directly or indirectly by acting as power for the light source (either heat or electricity). The light interacts with the analyte and is recorded by the photosensitive material. The nanosensors travel with the flood to the production well and are produced. At the surface, the nanosensors are recovered and analyzed.

The spectroscopic nanosensors can be included in drilling fluid. This application may be potentially advantageous in that the nanosensors would be ubiquitous throughout the well and (if very rugged) throughout the production lifetime of the well. If the light release step is sensitive to pressure and or temperature then once in place and triggered the sensor's record becomes indicative of the sensor's exact location along the well bore. If cement subsequently fails then recovery of the nanosensors could reveal the exact location of the breach. In a variation of this example, the nanosensors are circulated as part of the drilling fluid and they invade the nearby formations as part of the mud filtrate. As a casing is cemented in place, a trigger chemical is included in the cement slurry. While the cement is intact, there is no fluid flow from the formations into the borehole. If a cement failure occurs, any fluid flowing from the formation into the borehole will transport the nanosensors through the pores, voids or cracks in the cement. As the nanosensors pass through the cement, they are activated by the trigger chemical to capture spectroscopic information about the degraded cement. A monitor at the surface detects the nanosensors and extracts the spectroscopic information to aid in diagnosing cause and location of the failure. (Some of the temperature and pressure sensitive nanosensors can be included to provide the location information.)

Numerous variations and modifications will become apparent to those skilled in the art once the above disclosure is fully appreciated. For example, some reservoir sampling tools may be able to generate nanosensors on the spot by injecting (for example) a stable $H_2S$ reactive precipitate directly into the flow line and probing the precipitate later. It is intended that the following claims be interpreted to embrace all such variations and modifications.

What is claimed is:

1. A method of measuring formation properties, the method comprising:
   collecting nanosensors which have been transported from a formation via a fluid flow;
   measuring nanosensor states, the nanosensor states representing optical spectroscopy measurements recorded by the nanosensors before said collecting and while the nanosensors were contact with fluid of the formation; and
   reporting formation data derived from said spectroscopic measurements.

2. The method of claim 1, further comprising:
   introducing said nanosensors into said formation before said collecting.

3. The method of claim 2, further comprising:
   causing the nanosensors to emit light while in said formation, wherein said light interacts with an environment around said nanosensors and responsively causes a state change in the nanosensor.

4. The method of claim 3, wherein said causing includes transmitting an electromagnetic signal or an acoustic signal from a tool in a borehole proximate to the formation.

5. The method of claim 3, wherein said causing includes providing a time-release membrane that allows a photoluminescent reaction to occur after a predetermined delay.

6. The method of claim 3, wherein the state change occurs in a photosensitive molecule.

7. The method of claim 6, wherein the photosensitive molecule is provided with a narrowband sensitivity via a chromophore.

8. The method of claim 1, wherein said measuring includes using a filter or centrifuge to separate the nanosensors from the fluid.

9. The method of claim 8, wherein said measuring further includes probing photosensitive materials in the nanosensors with electron spin resonance.

10. The method of claim 8, wherein said measuring further includes optically examining photosensitive materials in the nanosensors.

11. The method of claim 8, wherein said reporting includes measuring luminescence of the nanosensors and deriving formation spectra based at least on the measured luminescence and the measured nanosensor states.

12. The method of claim 2, wherein said introducing includes circulating the nanosensors in a borehole fluid.

13. The method of claim 2, wherein said introducing includes suspending the nanosensors in a flood fluid.

14. The method of claim 2, wherein said introducing includes injecting the nanosensors into an isolated portion of a borehole wall.

15. The method of claim 4, wherein said electromagnetic or acoustic signal targets a particular azimuth.

16. The method of claim 4, wherein said electromagnetic or acoustic signal targets a particular radial distance.

17. A system for measuring formation properties, the system comprising:
   a carrier fluid that conveys nanosensors into a borehole to record optical spectroscopy measurements while the nanosensors contact and penetrate a formation,
   wherein at least some of the nanosensors include photosensitive materials, and
   wherein at least some of the nanosensors include luminescent materials.

18. The system of claim 17, Wherein the luminescent materials are triggerable by a time delay or an external signal.

19. The system of claim 18, wherein the luminescent material includes diamond with nitrogen vacancies that fluoresce in response to electromagnetic signal pulses.

20. The system of claim 17, wherein at least some of the nanosensors are coated to provide a surface affinity for interacting with a target material in the formation.

* * * * *

UNITED STATES PATENT AND TRADEMARK OFFICE
CERTIFICATE OF CORRECTION

| | | |
|---|---|---|
| PATENT NO. | : 8,921,768 B2 | Page 1 of 1 |
| APPLICATION NO. | : 13/636294 | |
| DATED | : December 30, 2014 | |
| INVENTOR(S) | : Christopher M. Jones et al. | |

It is certified that error appears in the above-identified patent and that said Letters Patent is hereby corrected as shown below:

In the Specification

In line 12 of column 5, the word "ofpboLobnxdocmconcc" should be replaced with --of photoluminescence--.

In line 64 of column 6, the words "pro vide" should be replaced with --provide--.

In line 36 of column 7, the word "hulk" should be replaced with --bulk--; in line 41 of column 7, the word "IV" should be replaced with --HF--.

In line 1 of column 8, the word "spectra" should be replaced with --spectral--.

In the Claims

In line 8 of claim 1, the word --in-- should appear between the words "were contact".

Signed and Sealed this
Twenty-eighth Day of July, 2015

Michelle K. Lee
*Director of the United States Patent and Trademark Office*